United States Patent [19]
Ghilardi et al.

[11] 3,980,769
[45] Sept. 14, 1976

[54] SHAMPOO CONTAINING A WATER-SOLUBLE CATIONIC POLYMER

[75] Inventors: Giuliana Ghilardi; Claire Fiquet, both of Paris, France

[73] Assignee: L'Oreal, Paris, France

[22] Filed: Sept. 4, 1973

[21] Appl. No.: 394,346

[30] Foreign Application Priority Data
Sept. 5, 1972  Luxemburg............................ 65997

[52] U.S. Cl................................ 424/70; 252/DIG. 2; 252/DIG. 3; 252/DIG. 13; 252/544; 252/545; 252/546; 252/547; 252/550; 252/551; 424/DIG. 2; 424/71; 424/78; 424/81
[51] Int. Cl.$^2$........................................... A61K 7/06
[58] Field of Search.............. 424/DIG. 2, 70, 71; 252/DIG. 2, DIG. 3, DIG. 13, 544, 545, 546, 547, 550, 551; 260/78 SC, 80.3 N, 80.72

[56] References Cited
UNITED STATES PATENTS

| | | |
|---|---|---|
| 2,882,185 | 4/1959 | Valko et al. ................ 260/78 SC X |
| 2,926,116 | 2/1960 | Keim........................... 260/78 SC X |
| 2,926,154 | 2/1960 | Keim........................... 260/78 SC X |
| 3,361,718 | 1/1968 | Fujimoto et al. .......... 260/89.7 N X |
| 3,769,398 | 10/1973 | Hewitt................................. 424/70 |
| 3,849,548 | 11/1974 | Grand................................. 424/70 |

Primary Examiner—Sam Rosen
Assistant Examiner—Vera C. Clarke
Attorney, Agent, or Firm—Cushman, Darby & Cushman

[57] ABSTRACT

An aqueous detergent composition usefully employed as a hair shampoo formulation consists essentially of at least one anionic surface-active agent, at least one of an amphoteric (zwitterionic) or polar nonionic surface-active agent and a water-soluble nitrogen-containing polymer having a molecular weight of 2,000–5,000,000.

14 Claims, No Drawings

SHAMPOO CONTAINING A WATER-SOLUBLE CATIONIC POLYMER

This invention relates to an aqueous detergent composition which is especially suitable for cleansing hair and which exhibits controlled detergency characteristics.

A shampoo composition for cleansing hair should have certain essential characteristics. For example, it not only should have good wetting, foaming and detergent properties so as to assure satisfactory cleaning of the hair, but its detergent power should be so controlled so as to avoid the removal of substantial proportions of the natural oil of the hair. Further, it is important that after a shampooing operation the hair be supple and easy to set and that the thus treated hair exhibit excellent set retention characteristics.

Thus, it is an object of the present invention to provide a stable aqueous detergent composition exhibiting controlled detergency characteristics and good foaming power so as to assure excellent conditioning of the hair, great ease in combing out wet and dry hair, improved hair softness and suppleness so as to facilitate the setting of the hair and a notable improvement in set retention.

The aqueous detergent composition of the present invention comprises (a) one or more anionic surface-active agents, (b) at least one amphoteric and/or zwitterionic and/or polar nonionic surface-active agent, and (c) a water-soluble nitrogen-containing cationic polymer.

Heretofore, detergent compositions containing polymeric components have been known. Included in these known compositions are those described, for instance, in U.S. Pat. Nos. 3,313,734 and 3,400,198; and French Patents 1,588,952 and 2,077,417 and British Patent 1,078,075.

The detergent composition according to the present invention as indicated above also contains polymeric components and exhibits good foam starting characteristics, excellent foaming power, limited detergency power that can be carefully calculated so as to avoid excessive degreasing of the hair and it assures good conditioning of the hair.

Since the anionic surface-active agent component of the composition of this invention constitutes the essential detergent and foaming component of this composition, it has a pronounced anionic character. The anionic surface-active agent can be a water-soluble salt, particularly the sodium, ammonium or ethanolamine salt of alkylsulfates, alkylethersulfates, alkylglycerylether sulfonates, sulfates and sulfonates produced by the reaction of one mole of an alcohol having from 12 to 18 carbon atoms with 2 to 3 moles of ethylene oxide; the condensation product of fatty acids with taurine or its derivatives, sarcosine or its derivatives and isethionates; as well as condensation product of fatty acids with polypeptides, alkylsulfosuccinates, and the like.

Preferably, alkylsulfates, alkylethersulfates, N-acyl sarcosinates, and sulfosuccinates are used as anionic surface-active agent. The proportion of the anionic surface-active agent employed is generally between 5 and 50 and, preferably, between 5–25 and more preferably between 10–15.5 weight percent of the total weight of the composition.

As indicated above, the anionic surface-active agent is employed in combination with an amphoteric and/or zwitterionic surface-active agent and/or a polar nonionic surface-active agent in the detergent composition of this invention.

The amphoteric and/or zwitterionic surface-active agent used can easily be prepared by known processes such as, for example:

1. by the condensation of a halogeno-alkanecarboxylic acid, preferably a chloro- or bromo- acetic or propionic acid on a primary, secondary or tertiary fatty amine, or, alternatively by the reaction of a halogenated diacid, such as chlorosuccinic acid, on said amine;
2. by the condensation of an amino acid on an alkyl halide or on a chloromethyl ether derived from a higher alcohol, or again on a fatty chain epoxide;
3. by the condensation of a primary, secondary or tertiary amine, including heterocyclic amines, such as pyridine, on α-halogenated fatty acids;
4. by the addition of a primary or secondary fatty amine on an activated double-bond acid compound such as, for example, acrylic acid or acids derived from maleamic acid in accordance with the procedures set forth in French Patent No. 1,344,212, preferably from compounds having the formula:

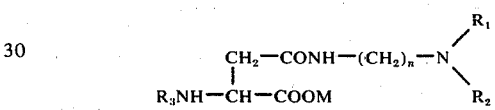

wherein $R_1$ and $R_2$ are methyl, ethyl, hydroxymethyl, hydroxyethyl, $R_3$ is an alkyl of 10 to 18 carbon atoms and M is hydrogen, sodium, potassium or ammonium.

5. by the condensation of chloroacetic acid on an secondary amine containing a quaternary group.
6. by the condensation of a halogeno alkane carboxylic acid, such as chloroacetic acid, on an alkyl thioether, for example, dodecyl/and/methyl sulfide.

Preferably, substituted betaines are employed, such as alkyl dimethylammonio acetate of the formula:

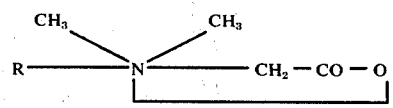

wherein R is alkyl of 12–18 carbon atoms; or amidoalkyl betaine of fatty acids of the formula:

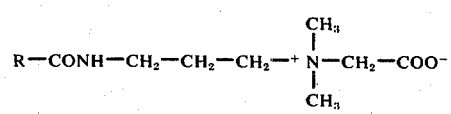

wherein R is alkyl of 7 to 17 carbon atoms.

As the polar nonionic surface-active agent there is preferably employed an amine oxide of the formula $R_1R_2R_3N \longrightarrow O$, wherein $R_1$ is alkyl, alkenyl or monohydroxyalkyl, having from 10 to 16 carbon atoms; $R_2$ and $R_3$ each independently represent methyl, ethyl, propyl, hydroxyethyl and hydroxypropyl. Preferably, dodecyldimethylamine oxide is employed.

The amphoteric or zwitterionic and/or polar nonionic surface-active agent is present in amounts relative to the total weight of the composition, between 0.5 and 4.9 and, preferably, between 2.5 and 4.9 weight percent thereof.

The ratio by weight of amphoteric or zwitterionic and/or polar nonionic surface-active agent: anionic surface-active agent is between 1:15 and 1:2 and preferably between 1:8 and 1:3.

The presence of the amphoteric or zwitterionic and/or polar nonionic surface-active agent notably improves the starting and stability of the foam and provides an increase in the foaming power of the detergent composition. The amphoteric and/or zwitterionic and/or nonionic surface-active agents exhibit, in combination with the anionic surface-active agent, within very precise limits of concentration, a very considerable foam synergism, generally in the order of about 10 to 40%.

This combination of surface-active agents also provides controlled, i.e. limited detergency power of the resulting composition. Thus, it not only assures the avoidance of the removal of substantial amounts of the natural oil of the hair but by varying the ratio between the anionic surface-active agent to the zwitterionic and/or polar nonionic surface-active agent, it is possible to obtain a series of compositions having a more or less considerable detergent power for the same foaming power. This ratio can accordingly be varied according to the desired purpose and objective of the resulting detergent composition. Further, this particular combination of surface-active agents due to its substantivity for keratin provides improved compatibility with the hair and consequently an improvement of the state of the hair after having shampooed with the composition of this invention. Moreover this particular combination of surface-active agents reduces in a notable way, the aggressiveness of the resulting composition and therefore increases the epidermic and ocular tolerance of the latter. The cationic polymer, due to its substantivity for keratin fibres, improves the cosmetic condition of the hair, namely its softness, the ease with which it can be combed out, its shine and its suppleness. It also gives the hair more "body" and more springiness, and thus makes sets stay in longer, and gives "bulk" and volume to the head of hair. The concentration, by weight, of the cationic polymer is suitably 0.05 to 4%, and preferably 0.25 to 1.5% by weight of the total weight of the composition.

The cationic polymer employed in the composition of this invention is soluble in water and compatible with the anionic-amphoteric and/or zwitterionic and/or polar nonionic surface-active agent combination described above and has a molecular weight of 600 to 5,000,000, with 10 to 50% of its molecular structure comprising one or more quaternary ammonium groups, the remainder being made up of non-quaternized polymer units.

The preferred molecular weights are between 600 and 6,000; 10,000 and 1,500,000.

The degree of quaternization is not greater than 50% so as to reduce or essentially avoid incompatibility with the above described anionic surface-active agent.

The water-soluble nitrogen-containing cationic polymer employed is selected from the group consisting of
  i. polyamide-polyamine polymers having recurring units of the formula:

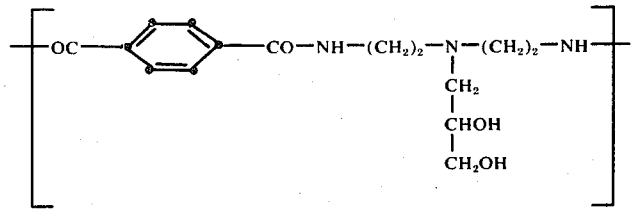

generally between 2 and 20 such units, said polymer being the polycondensation product of methyl terephthalate and diethylene triamine and alkylation product thereof with glycidol;
  ii. quaternary copolymer of vinylpyrrolidone comprising as structural groups:
    a. 40–90 mole percent vinylpyrrolidone,
    b. 5–40 mole percent dialkyl lower aminoalkyl acrylate or methacrylate, or dialkyl lower aminohydroxyalkyl acrylate or methacrylate and,
    c. 0–50 mole percent vinyl monomer copolymerizable with vinylpyrrolidone.

Preferably the water-soluble nitrogen-containing cationic polymer has a molecular weight between about 100,000 and 1,000,000, such as the commercial products "Gafquat 734" and "Gafquat 755" sold by the GAF corporation.

In general, these quaternary copolymers can be prepared by subjecting a solution of vinylpyrrolidone and the amino acrylate or methacrylate monomer, with or without the optional copolymerizable vinyl monomer, to conditions leading to a vinyl polymerization by a double bond. Thus, for example, polymerization can be suitably initiated by the action of free radicals, using for instance free radical forming catalysts such as organic and inorganic peroxides, such as hydrogen peroxide, tertiary butyl peroxide, and the like or azo aliphatic compounds, such as azobisisobutyronitrile. Obviously other free radical forming catalysts that are well known in the polymerization art can also be employed.

Preferably, polymerization is performed in solution at temperatures varying from about 50°C to 100°C or more, or even at a temperature between about 15° and 85°C. Preferably, the copolymerization reaction is carried out in the absence of free oxygen, suitably under an atmosphere of an inert gas such as nitrogen, argon or other similar gas, or at atmospheric pressure.

Quaternization of the tertiary amino group of said polymers and copolymers can be obtained by using a standard quaternization agent such as dialkyl sulfates, for example, dimethyl sulfate, diethyl sulfate and the like, an alkylsulfonic acid, for example, methylsulfonic acid, ethylsulfonic acid and the like, benzyl halides, such as, benzyl chloride, benzyl bromide, benzyl iodide, and the like as well as an alkyl halide. Other standard quaternization agents can also be employed.

The quaternary copolymers of vinylpyrrolidone may be represented by the formula:

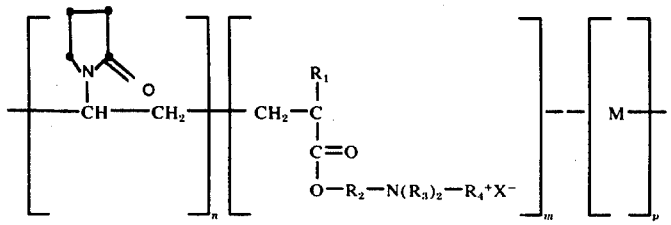

in which n represents 40 to 90 mol %, m represents 5 to 40 mol %, p represents 0 to 50 mol %, with $n + m + p = 100\%$, $R_1$ represents H or $CH_3$; $R_2$ is $CH_2$-CHOH-$CH_2$ or $C_xH_{2x}$ in which $x = 2$ to 18, $R_3$ represents $CH_3$ or $C_2H_5$, $R_4$ is $CH_3$, $C_2H_5$, X is Cl, Br, I, ½ $SO_4$, $HSO_4$ or $CH_3SO_3$, and M is a monomer unit resulting from the heteropolymerisation using any selected copolymerisable vinyl monomer.

The copolymers and process for preparing them are described in French patent 2.077.417, which describes acrylates or methacrylates of lower dialkyl aminoalkyl (or hydroxyalkyl) and M in the above formula.

The acrylates or methacrylates of lower dialkyl aminoalkyl (or hydroxyalkyl) suitable for producing the quaternary copolymers used in the compositions of the present invention comprise for example:

dimethylaminomethyl acrylate
dimethylaminomethyl methacrylate
diethylaminomethyl acrylate
diethylaminomethyl methacrylate
dimethylaminoethyl acrylate
dimethylaminoethyl methacrylate
dimethylamino-2-hydroxy-propyl acrylate
dimethylamino-2-hydroxy-propyl methacrylate
diethylamino-2-hydroxy-ethyl acrylate
diethylamino-2-hydroxy-ethyl methacrylate
dimethylaminobutyl acrylate
dimethylaminobutyl methacrylate
dimethylaminoamyl methacrylate
diethylaminoamyl methacrylate
dimethylaminohexyl acrylate
diethylaminohexyl methacrylate
dimethylaminooctyl acrylate
dimethylaminooctyl methacrylate
diethylaminooctyl acrylate
diethylaminooctyl methacrylate
dimethylaminodecyl methacrylate
dimethylaminododecyl methacrylate
diethylaminolauryl acrylate
diethylaminolauryl methacrylate
dimethylaminostearyl acrylate
dimethylaminostearyl methacrylate
diethylaminostearyl acrylate
diethylaminostearyl methacrylate The optional vinyl monomers represented by M in the above structural formula comprise all the standard vinyl monomers copolymerizable with N-vinylpyrrolidone. Thus, for example, of the suitable standard vinyl monomers, there can be recited alkylvinyl ethers, for example, methylvinyl ether, ethylvinyl ether, octylvinyl ether, etc.; acrylic and methacrylic acids and their esters, for example, methacrylate, methyl methacrylate, etc.; aromatic vinyl monomers, for example, styrene, x-methyl-styrene, etc.; vinyl acetate; vinylidene chloride acrylonitrile and its substituted derivatives; methacrylonitrile and its substituted derivatives; acrylamide and methacrylamide and their N-substituted derivatives; vinyl chloride, crotonic acid and its esters; etc.

The shampoo composition according to the present invention can be in the form of a clear, opaque or pearly solution or in the form of a cream, paste or gel. It can also include a conventional aerosol propellant, such as a fluorocarbon including for instance trichlorofluoromethane, dichlorodifluoromethane and 1,2-dichloro-1,1,2,2-tetrafluoroethane and be packaged under pressure in a conventional aerosol container as an aerosol.

The composition of this invention can also contain components and adjuvants usually used to obtain the appearance, color, odor, viscosity, pH and other desired specific characteristics of shampoo or detergent formulations, such as perfume, dye, foam stabilizer, opacifying agent, sequestering agent, superfatting agent, thickener or preservative agents.

The pH of the detergent composition of this invention can range from 6.5 to 9, preferably from 7.5 to 8.2.

| EXAMPLE 1 | |
|---|---|
| Sodium lauryl ether sulfate condensed with 2.2 moles of ethylene oxide | 15 g |
| 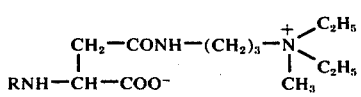 | 4.9 g |
| wherein R is the hydrocarbon radical derived from copra fatty acids. | |
| Quaternary copolymer of vinylpyrrolidone/ dialkyl lower aminoalkyl acrylate having a molecular weight of the order of 1,000,000 sold under the tradename "Gafquat 755" | 0.5 g |
| Water. q.s.p. | 100 g |
| pH = 7.5 | |

| -continued | |
|---|---|
| EXAMPLE 2 | |
| Monoethanolamine lauryl ether sulfate | 12 g |
| Triethanolamine N-acyl sarcosinate | 3.5 g |
| Alkyl dimethylammonio acetate sold under the tradename "Dehyton AB 30" (Alkyl = $C_{12}$–$C_{18}$) | 3 g |
| Quaternary copolymer of vinylpyrrolidone/ dialkyl lower aminoalkyl acrylate having a molecular weight of the order of 1,000,000 sold under the tradename "Gafquat 755" | 0.25 g |
| Water, q.s.p. | 100 g |
| pH = 8.2 | |
| EXAMPLE 3 | |
| Triethanolamine lauryl ether sulfate | 10 g |
| Alkyl dimethylammonio sulfate sold under the tradename "Dehyton AB 30" (Alkyl = $C_{12}$–$C_{18}$) | 2.5 g |
| Polymer having monomeric units of the formula: | |

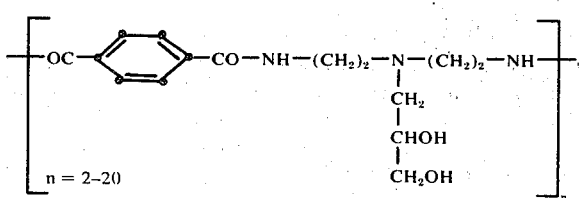

| | 1.5 g |
|---|---|
| water, q.s.p. | 100 g |
| pH = 7.8 | |

What is claimed is:

1. An aqueous detergent composition for use as a hair shampoo consisting essentially of
   a. at least one anionic surface-active agent in an amount of 5 to 50% by weight of the total composition
   b. at least one of an amphoteric surface active agent or polar nonionic surface-active agent, which polar nonionic is $R_1R_2R_3N$-O wherein $R_1$ is alkyl, alkenyl or monohydroxyalkyl of 10 to 16 carbon atoms, each of $R_2$ and $R_3$ is methyl, ethyl, propyl, hydroxyethyl or hydroxypropyl, in an amount of 0.5 to 4.9% by weight of the total composition and
   c. a water soluble nitrogen-containing polymer having a molecular weight between 600 and 5,000,000, said polymer being present in an amount of 0.05 to 4% by weight of the total composition and selected from the group consisting of
   i. polyamide-polyamine polymer having monomeric units of the formula

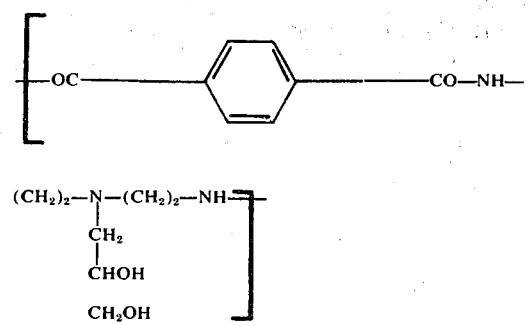

ii. vinylpyrrolidone quaternary copolymer having as structural groups:
   49–90 mole percent vinylpyrrolidone,
   5–40 mole percent dialkyl lower aminoalkyl acrylate or methacrylate, or dialkyl lower aminohydroxyalkyl acrylate or methacrylate, and
   0–50 mole percent a copolymerizable vinyl monomer.

2. The composition of claim 1 wherein said anionic surface-active agent is present in an amount of 5–25% by weight of the total composition.

3. The composition of claim 1 wherein said amphoteric or polar nonionic surface-active agent is present in an amount of 2.5–4.9% by weight of the total composition.

4. The composition of claim 1 wherein said water-soluble nitrogen-containing polymer is present in an amount of 0.25 to 1.5% by weight of the total composition.

5. The composition of claim 1 wherein the ratio of the amphoteric or polar nonionic surface-active agent to the anionic surface-active agent is between 1:15 and 1:2.

6. The composition of claim 1 wherein the ratio of amphoteric, or polar nonionic surface-active agent to the anionic surface-active agent is between 1:8 and 1:3.

7. The composition of claim 1 wherein the anionic surface-active agent is selected from the group consisting of the sodium, ammonium, and triethanolamine salt or an alkyl sulfate and an alkylether sulfate.

8. The composition of claim 1 wherein the amphoteric surface-active agent is a substituted betaine.

9. The composition of claim 1 wherein the polar nonionic surface-active agent is dodecyldimethylamine oxide.

10. The composition of claim 8 wherein said substituted betaine is alkyl dimethyl ammonio acetate, the alkyl moiety having from 12 to 18 carbon atoms.

11. The composition of claim 8 wherein said substituted betaine is fatty acid amido alkyl betaine.

12. The composition of claim 1 wherein the pH is 6.5–9.

13. The composition of claim 12 wherein the pH is 7.5–8.2.

14. The composition of claim 1, wherein the vinylpyrrolidone quaternary copolymer consists essentially of units having the structural groups:
   40–90 mole percent vinylpyrrolidone, and
   5–40 mole percent dialkyl lower aminoalkyl acrylate or methacrylate, or dialkyl lower aminohydroxyalkyl acrylate or methacrylate.

* * * * *